US009199007B2

(12) United States Patent
Julián Ibáñez et al.

(10) Patent No.: US 9,199,007 B2
(45) Date of Patent: Dec. 1, 2015

(54) USE OF GELLED PRP (PLATELET GEL) FOR VOLUMETRIC BREAST RECONSTRUCTION

(75) Inventors: Juan Francisco Julián Ibáñez, Cerdanyola del Valles (ES); Jorge Navinés López, Badalona (ES); Joan Ramon Grífols Ronda, Badalona (ES)

(73) Assignees: Banc De Sang I Teixits, Barcelona (ES); Fundacio Institut EN Ciencies De La Salut Germains Trias I Pujol, Badalona (ES); Universitat Autonoma De Barcelona, Cerdanyola Del Valles (ES)

( * ) Notice: Subject to any disclaimer, the term of this patent is extended or adjusted under 35 U.S.C. 154(b) by 0 days.

(21) Appl. No.: 13/377,293

(22) PCT Filed: Jun. 11, 2010

(86) PCT No.: PCT/EP2010/058226
§ 371 (c)(1),
(2), (4) Date: Dec. 9, 2011

(87) PCT Pub. No.: WO2010/142784
PCT Pub. Date: Dec. 16, 2010

(65) Prior Publication Data
US 2012/0087989 A1 Apr. 12, 2012

(30) Foreign Application Priority Data
Jun. 11, 2009 (ES) .................................. 200901433

(51) Int. Cl.
*A61K 35/16* (2015.01)
*A61L 27/54* (2006.01)
*A61L 27/22* (2006.01)

(52) U.S. Cl.
CPC .............. *A61L 27/54* (2013.01); *A61L 27/227* (2013.01); *A61L 2300/402* (2013.01); *A61L 2300/404* (2013.01); *A61L 2300/406* (2013.01); *A61L 2300/41* (2013.01); *A61L 2300/416* (2013.01)

(58) Field of Classification Search
None
See application file for complete search history.

(56) References Cited

U.S. PATENT DOCUMENTS

| 5,752,974 A * | 5/1998 | Rhee et al. ..................... 606/214 |
| 6,942,880 B1 | 9/2005 | Dolecek |
| 2004/0241146 A1 * | 12/2004 | Biscup .......................... 424/93.7 |
| 2006/0140923 A1 * | 6/2006 | Evangelista ............... 424/93.72 |
| 2007/0042016 A1 | 2/2007 | Nayak et al. |

FOREIGN PATENT DOCUMENTS

| EP | 1239895 | 9/2002 |
| WO | WO01/43787 | 6/2001 |

OTHER PUBLICATIONS

Man et al. "The use of autologous platelet-rich plasma (platelet gel) and autologous platelet-poor plasma (fibrin glue) in cosmetic surgery" Plastic Reconstructive Surgery 107: 229-237, 2001.*
Djohan et al. "Breast reconstruction options following mastectomy", Cleveland Clinic Journal of Medicine 75(1): S17-23, 2008.*
Smrke et al. "Allogeneic platelet gel with autologous cancellous bone graft for the treatment of a large bone defect", European Surgical Research 39: 170-4, 2007.*
Anitua et al. "Autologous platelets as a source of proteins for healing and tissue regeneration", Thrombosis and Haemostasis 91: 4-15, 2004.*
PCT Search Report for PCT/EP2010/058226, completed Feb. 16, 2011.

* cited by examiner

*Primary Examiner* — Taeyoon Kim
*Assistant Examiner* — Emily Cordas
(74) *Attorney, Agent, or Firm* — Barnes and Thornburg LLP

(57) ABSTRACT

The present invention relates to the application of a platelet gel for augmenting or restoring the volume of a soft tissue, particularly breast tissue, to biological implants comprising said gel, to a kit for preparing said implants and to a process for preparing said implants.

23 Claims, No Drawings

USE OF GELLED PRP (PLATELET GEL) FOR VOLUMETRIC BREAST RECONSTRUCTION

CROSS-REFERENCE TO RELATED APPLICATIONS

This application is a U.S. national counterpart application of PCT International Application Serial No. PCT/EP2010/058226, filed Jun. 11, 2010, which claims priority to Spanish Patent Application Serial Number P200901433, filed Jun. 11, 2009, the disclosures of both of which are hereby incorporated herein by reference.

TECHNICAL FIELD

The present invention relates to the field of reconstruction and augmentation of soft tissue, particularly breast tissue.

STATE OF THE ART

Growing awareness of breast cancer, along with improved diagnosis techniques, allow to get diagnosis at very early stages. Thus, an increasing number of non-invasive techniques that avoid mastectomy and are limited to the excision of the tumour (tumorectomy) with wide resection margins can be applied. In spite of this, even in these cases of minimally invasive surgery, the occurrence of aesthetical defects due to the cavity left by the tumorectomy, which is an empty space that does not maintain the volume of the organic structure, is frequent. Additionally, there are still several situations wherein it is not possible to avoid mastectomy, for example when the tumour has a disproportionate size with respect to breast volume or in the case of unilateral multicentric tumours.

Synthetic breast implants or autologous reconstruction (i.e. reconstruction using the patient's own tissue) are used for the reconstruction of breasts subjected to tumorectomy or mastectomy or for breast augmentation.

The main types of artificial implants consist of a silicone capsule filled with silicone gel or saline solution. Combined implants have also been disclosed in the literature, such as that disclosed in EP-A-797460, which uses matrices seeded with cells, preferably muscle cells.

In autologous reconstructions, abdominal adipose skin and tissue and part of the straight abdominal muscles are normally used. Alternatively, latissimus dorsi musculocutaneous flap tissue has also been used.

In order to fill up tumorectomy cavities, other techniques such as oncoplastic techniques are also used, which are aimed at improving the patient's appearance by remodelling the remaining gland itself (remaining gland technique).

Both autologous reconstructions and artificial implants have several drawbacks. On one hand, the problems associated with said artificial implants include deflation, infection, capsular contracture, displacement and formation of calcium deposits. On the other hand, the aforementioned autologous implants provide generally acceptable aesthetical results but with a not inconsiderable morbidity. Additionally, the scars that appear on the donor site and the potential increase for complications must also be taken into account (Cleveland Clinic Journal of Drug 2008; 75(1): S17-S23). A high number of resorptions have also been disclosed.

The use of silicone implants in other areas, such as the glutei, has also been disclosed.

Platelets play a basic role in the wound repair process, regardless of their aetiology. When a wound occurs, the platelets become activated and release diverse growth factors, such as PDGF (platelet-derived growth factor), EFT (epidermal growth factor) and TGF (transforming growth factor), which converts fibrinogen into fibrin, forming a cross-linking that finally gives rise to a clot.

Activation of a platelet concentrate (PRP) by adding a clotting cascade activator, such as an excess of calcium ions (calcium chloride), thrombin, batroxobin, etc., gives rise to the formation of a gelatinous substance known as platelet gel.

At present, platelet gel is widely used in dental and oral and maxillofacial surgery, where it is used basically for bone implantation and regeneration. It is also applied to chronic wounds, ulcers and soft tissues (such as tendons and ligaments). A layer is generally spread over the wound bed to aid healing. Its use in facial plastic surgery and breast augmentation and reduction operations as a sealant and haemostatic agent has been disclosed, where it reduced the need for drainage and compressive bandaging as well as the incidence of complications (Acta Dermatoven APA Vol. 16, 207, No. 4).

However, the results of a double-blind randomized trial to evaluate the topical application of autologous platelet gel in reduction mammoplasty did not reveal any significant improvement due to the use of the gel (Plastic and Reconstructive Surgery (2007), 119(4), 1159-1166).

Different methods and kits for preparing platelet gel have been disclosed, for example, in U.S. Pat. No. 6,942,880. This patent, among several embodiments, mentions that optionally the autologous platelet gel can be moulded into a geometric, rectangular, conical or roller shape to temporarily fill, by way of a plug, cavities due to dental extraction or bone cavities. Although it does not explicitly indicate what can be considered a temporary filling, it does indicate that, for example, another bioadhesive sealant formed by clotting of fibrinogen with thrombin is reabsorbed in just ten days. In the only example provided, the gel is prepared from just 6 $cm^3$ of PRP.

OBJECT OF THE INVENTION

The problem to be solved by the present invention is the provision of a drug or biological implant to be implanted in a soft tissue, preferably a breast, for reconstruction or augmentation of the volume of said tissue, that will overcome the drawbacks of the state of the art.

The solution is based on the fact that the present inventors unexpectedly found that the use of conveniently moulded platelet gel allows the re-establishment of soft tissue volume over time (see example 3). In particular, the inventors verified this upon introduction into a cavity produced by tumorectomy in a breast, obtaining good results even using large volumes, for example 250 $cm^3$, so that it can be used by way of a biological implant such as a breast implant.

The present inventors have achieved the volumetric substitution of removed tissue using the platelet gel, favoring internal scarring and improving the aesthetical result without increasing surgical morbidity, as well as augmenting breast volume.

Therefore, a first aspect of the invention relates to the use of a platelet gel for preparing a drug or a biological implant to be implanted in a soft tissue for reconstruction, augmentation or correction of abnormalities in the size and shape of said soft tissue, characterized in that said drug or biological implant comprises a platelet gel.

Alternatively, this first aspect of the invention can be worded as platelet gel for use as a biological implant to be implanted in a soft tissue for reconstruction, augmentation or correction of abnormalities in the size and shape of said soft tissue.

The second aspect of the invention relates to a biological implant for soft tissue comprising a platelet gel.

A third aspect of the invention relates to a kit for preparing a biological implant according to the present invention, comprising

- at least one mould in the shape of a round concave receptacle with a volume comprised between 75 and 700 cm$^3$,
- at least one syringe,
- one clotting activator, and
- optionally, one drug.

A fourth aspect of the invention relates to a process for preparing the biological implant, in accordance with the present invention, comprising the following steps:

(i) Combining a platelet-rich plasma with a clotting activator and, optionally, a drug, (ii) Heating the mixture in a mould in the shape of a round concave receptacle with a volume comprised between 75 and 700 cm$^3$ at a temperature from 30° C. to 40° C., in order to achieve the gelling of said mixture.

The use of the platelet gel, in accordance with the present invention, represents a number of advantages:

It avoids the use of artificial materials and the risks deriving from its use, such as infections, diffusion or displacements;

It enhances the restructuration of the remaining healthy breast tissue, taking advantage of the fact that the substances released by the platelets, such as growth factors, initiate and accelerate tissue repair and regeneration.

Additionally, the use of platelet gel, in accordance with the invention, is particularly advantageous in tumorectomy and mastectomy operations:

It allows remodeling the breast during the same surgical operation as the mastectomy and/or subcutaneous mastectomy, avoiding other oncoplastic techniques which require a subsequent or more complex surgical operation and the potential complications thereof;

It minimizes the anti-aesthetic retractions susceptible from more complex surgical operations;

It can facilitate selective radiotherapy on distending the residual cavity;

The fact that the gel can be prepared in situ allows to have greater flexibility for preparing any desired volume, based on the tumour volume calculated after extraction, advantageously for tumorectomies, as opposed to artificial silicone implants of a determined size.

It allows the application of a preserving surgical treatment (tumorectomy) to larger size tumours that were previously only candidates for mastectomy due to being disproportionate to the size of the breast;

It allows the application of the preserving surgical treatment (tumorectomy) to unilateral multifocal tumours that were previously only candidates for mastectomy due to aesthetic reasons.

It allows to improve the identification of relapses, preventing differentiation of residual scars;

It does not alter the monitoring protocol by means of mammography, ecography or NMR (Nuclear Magnetic Resonance);

It improves the appearance of the patient, allowing a faster incorporation into the job market;

It reduces the costs of the reconstruction processes required for this type of surgery.

DETAILED DESCRIPTION OF THE INVENTION

Platelet Gel

Platelet gel is obtained from platelet-rich plasma (PRP) whereto a clotting process-activating substance (for example, calcium chloride) is added.

PRP, as used herein, is understood to be a concentration of platelets greater than the concentration in peripheral blood suspended in a plasma solution. PRP typically has a minimum platelet count of $7.5 \times 10^5 - 1 \times 10^6$ per μL.

Biological implant, as used herein, is understood to be a product of substantially biological origin for the replacement or augmentation of a missing or imperfect part of the body.

Preparation of Platelet Gel

The platelet dosage required for preparing the platelet gel can be obtained by means of plateletpheresis. Plateletpheresis comprises extraction and separation of blood into its different components by centrifugation at different speeds for the purpose of obtaining platelet-rich plasma (PRP).

PRP can be obtained from the same patient whom the gel (autologous platelet gel) will be implanted or from a healthy allogeneic donor. In the event that the gel will be used for the reconstruction of a breast already subjected to tumorectomy or mastectomy, the platelets are obtained from a healthy allogeneic donor, optionally related to the patient.

Plateletpheresis can be carried out, for example, using the HAEMONETICS™ MCS+ cell separator or MEDTRONIC® Inc.'s MAGELLAN™ Autologous Platelet Separation System.

During the plateletpheresis process an anticoagulant is added preferably based on citric acid, such as ACD-A (citric acid, sodium citrate and dextrose).

In general, PRP is required to have a minimum platelet count of $7.5 \times 10^5 - 1 \times 10^6$ per μL.

When the PRP is obtained from an allogeneic donor it is preferably treated by irradiation to deactivate any existing viral material or residual leukocyte. This treatment can be carried out during any stage of the gel preparation process.

The PRP is activated by adding a clotting activator, which is understood to be a substance capable of restoring anti-clotting activity, such as calcium chloride or other calcium salt which acts in a similar way, such as calcium gluconate or calcium carbonate. Preferably, calcium chloride is added as a 105 by weight aqueous solution.

Other clotting activators can also be used, including thrombin or batroxobin, by heating the mixture at 37° C.

The platelet gel can also be obtained by means of the processes disclosed in literature, such as those disclosed in EP-B-1239895, which use batroxobin instead of thrombin.

The PRP volume to be used is determined based on the final volume to be augmented or restored. Preferably, a correction factor comprised between 1.6 and 2.2 is applied. The mixture is allowed to clot in a sterilised mould having adequate dimensions. The mould can be made, for example, of ceramic, plastic, silicone glass or stainless steel. Preferably, it is allowed to clot in a sterile porcelain or stainless steel receptacle. More preferably, a porcelain mould is used.

The shape of the mould in general is such that the resulting gel adopts the desired shape of the implant. The mould is preferably formed in the shape of a round concave receptacle with a volume comprised between 75 and 700 cm3. In one embodiment of the invention, the mould has a substantially semispherical shape. In a preferred embodiment, the shape of the mould is such that the resulting gel takes the form of a breast implant with different volumes.

Preferably, the platelet gel for implantation, in accordance with the invention, has a volume comprised between 25 and 600 cm3.

Formation of the gel is fast, generally being formed in less than fifteen minutes.

The platelet gel can optionally be used to release drugs such as antibiotics, anti-bacterials, analgesics, anti-inflammatories, anti-cancer compounds and tumoricidal or tumor static compounds. These compounds can be added to the PRP before adding the calcium salt. In one embodiment of the invention, the PRP is added to an antibiotic, such as Cloxacillin. Preferably, the antibiotic is selected from the group formed by betalactamic antibiotics. When an antibiotic is added, it is preferably added at a concentration ten times greater than that of the plasma.

In a preferred embodiment, the platelet-rich plasma (PRP) obtained is mixed with an adequate amount of a 10% by weight calcium chloride solution and is heated at 37° C., for example in bain-marie, preferably in a sterile ceramic receptacle, until gelling. This clotting process may take approximately between 4 and 10 minutes, depending on gel volume, among other factors.

Platelet activation initiates the platelet degranulation process, releasing diverse growth factors, such as PDGF (platelet-derived growth factor), EGF (epidermal growth factor) and TGF (transforming growth factor) and converts the fibrinogen into fibrin, forming a cross-linking that finally gives rise to the clot.

In a preferred embodiment of the invention, the platelet gel preparation process, in accordance with the fourth aspect of the invention, also comprises the following subsequent steps:

Cooling the gelled mixture, preferably at room temperature, to give rise to the formation of a liquid phase differentiated from the gel phase, and Isolation of the gel phase obtained in the previous step.

Use of the Platelet Gel

In accordance with the present invention, the platelet gel is used to prepare a drug or biological implant to be implanted in a soft tissue for reconstruction, augmentation or correction of abnormalities in the size and shape of said soft tissue, characterized in that said drug or biological implant comprises a platelet gel. Said drug or biological implant can be constituted by, for example, more than 50% by weight of the platelet gel, or more than 70% or more than 90%. Preferably, said drug or biological implant essentially consists of a platelet gel. More preferably, said drug or biological implant consists of a platelet gel.

The platelet gel molded in accordance with the invention can be surgically implanted following the processes known in the state of the art; for example, those used for silicone gel implants, particularly in the case of a breast biological implant, it may be implanted at subglandular or subpectoral level.

Preferably, the platelet gel is used just after its clotting, in order to take maximum advantage of the benefits of releasing the growth factors that accompany the clotting process.

The soft tissue wherein the biological implant or drug is implanted, in accordance with the invention, is preferably selected from the group consisting of breast, gluteal, abdominal and facial tissue. More preferably, it is selected from breast, gluteal and abdominal tissue. Even more preferably, it is implanted in a breast.

Preferably, the platelet gel is used for the reconstruction of a breast subjected to tumorectomy. In this case, the PRP volume to be used to prepare the platelet gel can be calculated based on the tumour volume, which can be measured or calculated by means of the liquid displaced by the tumour itself, according to Archimedes' Principle. After calculating the tumour volume, a variable correction factor (between 1.6 and 2.2) is preferably applied in order to determine the volume of platelet gel to be implanted. The volumetric control can be obtained by comparing the pre- and post-operative breast volumes by means of volumetric measurement using Nuclear Magnetic Resonance.

When the patient has been subjected to tumorectomy or mastectomy, the platelet gel is prepared from PRP obtained from a healthy allogeneic donor.

Biological Implant

The biological implant for soft tissue, in accordance with the second aspect of the invention, comprises a platelet gel. Said biological implant can be constituted by, for example, more than 50% by weight of the platelet gel, or more than 70% or more than 90%. Preferably, said biological implant essentially consists of a platelet gel. More preferably, said biological implant consists of a platelet gel.

Preferably, the biological implant according to the invention has a volume comprised between 25 and 600 $cm^3$.

The implant, in accordance with the invention, can be a breast, gluteal, abdominal or facial implant, preferably a breast, gluteal or abdominal implant. More preferably, said biological implant is a breast implant.

Kit for Preparing the Biological Implant

The present invention also provides a kit for facilitating the preparation of the biological implant, in accordance with the present invention, comprising:

a mould in the shape of a round concave receptacle with a volume comprised between 75 and 700 $cm^3$, at least one syringe one clotting activator, and optionally, a drug.

In a preferred embodiment, said kit also comprises a bag containing platelet-rich plasma. Preferably, the clotting activation agent used in said kit is an aqueous solution of 10% calcium chloride. In one embodiment of the invention, said kit contains at least one pre-filled syringe containing said calcium chloride solution.

Several examples of the invention are shown below in an illustrative non-limiting way.

EXAMPLES

Example 1

Production of Platelet-Rich Plasma (PRP)

The PRP was obtained from healthy allogeneic patients following a plateletpheresis process. Plateletpheresis was carried out using the HAEMONETICS™ MCS+ cell separator.

ACD-A was used as anti-coagulant.

The PRP obtained had a minimum platelet count of $7.5 \times 10^5 - 1 \times 10^6$ µL.

Plateletpheresis was carried out the day before the surgical operation.

Example 2

Preparation of the Platelet Gel

The volume of PRP to be used to form the platelet gel was calculated based on the volume of the tumour of each patient by means of the volume displaced by the tumorectomy piece immersed in saline solution in a test tube. A correction factor of approximately 1.6 was then applied.

The PRP volumes used for each patient under study are shown in Table 1.

In each case, a 10% by volume of an aqueous solution of 10% by weight calcium chloride was added to the volume of platelet-rich plasma (PRP) and mixed.

The mixture was heated at 37° C. in bain-marie in a sterile ceramic receptacle until it gelled.

In general, the clotting process took approximately between 4 and 10 minutes.

In some cases, the process was accelerated by adding human thrombin.

Example 3

Breast Reconstruction Using Platelet Gel

A sample was taken from 19 patients, four forming the control group and 15 the cases under study.

The patients were women with unilateral breast neoplasia who were candidates for preserving treatment.

Those patients who fulfilled any of the following exclusion criteria were excluded: treatments with anti-coagulants, primary clotting and/or scarring alteration and breast infection at the time of the surgical operation.

In the fifteen cases under study, the patients were subjected to tumorectomy in a breast with wide margins and immediate volume reconstruction using platelet gel, obtained in accordance with Example 2.

The patients of the control group were subjected to tumorectomy in a breast without any kind of volumetric reconstruction.

Example 4

Comparative Analysis of Patients Subjected to a Breast Neoplasia Operation with and without Volume Reconstruction Using Platelet Gel In order to evaluate the result of the use of the platelet gel for breast reconstruction in patients subjected to a breast neoplasia operation, they were given a questionnaire to evaluate their degree of satisfaction and digital photographs were taken at different times (pre-operative, immediate post-operative and after one, three months, six months and one year).

Table 1 shows the tumorectomy volumes and the platelet gel volume added for breast reconstruction, and reflects the results of the post-operative volumetric appearance in relation to the pre-operative volumetric appearance at different times.

TABLE 1

| PATIENT | TUMOUR VOLUME ($cm^3$) | PRP VOLUME ($cm^3$) | POST-OPERATIVE APPEARANCE | | | |
|---|---|---|---|---|---|---|
| | | | IMMEDIATE | 1 week | 1 month | 3 months |
| 01 | 90 | 110 | VG | VG | VG | G |
| 02 | 40 | 60 | VG | VG | VG | VG |
| 03 | 30 | 45 | VG | VG | VG | VG |
| 04 | 50 | 40 | VG | VG | VG | VG |
| 05 | 30 | 50 | VG | VG | VG | VG |
| 06 | 33 | 40 | VG | VG | VG | |
| 07 | 70 | 105 | VG | VG | VG | |
| 08 | 75 | 105 | VG | VG | G | |
| 09 | 44 | 104 | VG | VG | A | |
| 10 | 30 | 80 | VG | VG | VG | |
| 11 | 80 | 140 | VG | VG | VG | |
| 12 | 70 | 100 | VG | VG | VG | |

TABLE 1-continued

| PATIENT | TUMOUR VOLUME ($cm^3$) | PRP VOLUME ($cm^3$) | POST-OPERATIVE APPEARANCE | | | |
|---|---|---|---|---|---|---|
| | | | IMMEDIATE | 1 week | 1 month | 3 months |
| 13 | 50 | 80 | VG | VG | B | |
| 14 | 45 | 60 | VG | VG | VG | |
| 15 | 160 | 250 | VG | VG | VG | |

VG = Very Good,
G = Good,
A = Average,
B = Bad,
VB = Very Bad

The criterion used to evaluate the results was a subjective criterion based on two observers. Therefore, it was defined as:

Very Good: identical or practically identical aesthetic result to that before the operation, Good: if the volume was preserved, Average: if any morphometrical deficiency was observed, the perimeter was not exactly the same but rather somewhat smaller, Bad: if evident excavation was observed, Very Bad: if retraction was observed.

Table 2 shows the tumorectomy volumes of patients subjected to a breast neoplasia operation without volume reconstruction using platelet gel as well as the results of the post-operative appearance in relation to pre-operative appearance at different times.

TABLE 2

| PATIENT | TUMOUR VOLUME ($cm^3$) | POST-OPERATIVE APPEARANCE | | | | |
|---|---|---|---|---|---|---|
| | | IMMEDIATE | 1 week | 1 month | 3 months | 6 months |
| 01 | 40 | VG | VG | G | A | |
| 02 | 70 | G | A | B | B | |
| 03 | 30 | VG | G | A | B | |
| 04 | 50 | G | G | B | | |

VG = Very Good,
G = Good,
A = Average,
B = Bad,
VB = Very Bad

The data shown in Table 1 reveal that the post-operative volumetric appearance in relation to the pre-operative appearance in patients subjected to a breast neoplasia operation with volume reconstruction using platelet gel remained satisfactory in most of the patients throughout the observed time periods. On the contrary, the data shown in Table 2 reveal that, in the case of patients not subjected to volume reconstruction using platelet gel, even though in some cases the appearance of the breast was apparently satisfactory immediately after the operation, one month after the operation the appearance of the breast was no longer satisfactory in most of them.

The photographs taken of the patients after the surgical operation show that, in most of the group of patients under study subjected to a breast neoplasia operation with volume reconstruction using platelet gel, after one month and, in five of them, several months after the operation, no deformation of the breast neither in the area surrounding the scar was observed, which had a clean appearance and completely smooth skin. While in the case of the control group, just one month after the operation the scar became retracted and sunken into the cavity left by the tumour, producing anti-aesthetic deformations.

With regard to the post-operative monitoring by radiological image (ecography, mammography and magnetic resonance), in one patient the appearance of macrocalcifications in the implant bed was observed which, on having a circumscribed arrangement, allows radiological monitoring thereof without considering differential diagnosis with other tumour sources.

The invention claimed is:

1. A method for volumetric substitution of a removed soft tissue from a patient, said method comprising the step of implanting a composition comprising a platelet gel in the patient,
   wherein the composition is a drug or biological implant,
   wherein the composition is implanted in the patient to replace the soft tissue removed from the patient,
   wherein the composition is implanted at a specific volume, and
   wherein the specific volume to be implanted is determined by applying a correction factor between 1.6 to 2.2 (volume of composition: volume of removed soft tissue).

2. The method of claim 1, wherein said drug or biological implant comprises more than 50% by weight of the platelet gel.

3. The method of claim 2, wherein said drug or biological implant consists essentially of the platelet gel.

4. The method of claim 1, wherein said soft tissue is selected from the group consisting of breast, abdomen and gluteus.

5. The method of claim 4, wherein said soft tissue is breast.

6. The method of claim 1, wherein said drug or biological implant further comprises at least one active ingredient selected from the group consisting of: antibiotics, anti-bacterials, analgesics, anti-inflammatories, anti-cancer compounds, and tumoricidal and tumour static compounds.

7. The method of claim 6, wherein said drug or biological implant further comprises an antibiotic.

8. The method of claim 1, for reconstruction of a breast which has been subjected to a tumorectomy.

9. The method of claim 8, wherein said platelet gel is prepared from platelet-rich plasma from a healthy allogeneic donor.

10. The method of claim 9, wherein the platelet gel is prepared from a volume of platelet-rich plasma comprised between about 1.6 and about 2.2 times the tumour volume.

11. The method of claim 9, wherein said platelet gel is obtainable from said platelet-rich plasma clotted by adding calcium chloride and by treating at about 37° C.

12. A method for augmentation of a soft tissue of a patient, said method comprising the step of implanting a composition comprising a platelet gel in the patient,
   wherein the composition is a drug or biological implant,
   wherein the composition is implanted in the patient to augment the soft tissue of the patient, and
   wherein the platelet gel is prepared from platelet-rich plasma from a healthy allogeneic donor.

13. The method of claim 12, wherein said drug or biological implant comprises more than 50% by weight of the platelet gel.

14. The method of claim 13, wherein said drug or biological implant consists essentially of the platelet gel.

15. The method of claim 12, wherein said soft tissue is selected from the group consisting of breast, abdomen and gluteus.

16. The method of claim 15, wherein said soft tissue is breast.

17. The method of claim 12, wherein said drug or biological implant further comprises at least one active ingredient selected from the group consisting of: antibiotics, anti-bacterials, analgesics, anti-inflammatories, anti-cancer compounds, and tumoricidal and tumour static compounds.

18. The method of claim 17, wherein said drug or biological implant further comprises an antibiotic.

19. The method of claim 12, wherein the soft tissue has been removed from the patient.

20. The method of claim 19, wherein the composition is implanted in the patient to augment the soft tissue that has not been removed from the patient.

21. The method of claim 12, wherein the platelet gel is prepared from a volume of platelet-rich plasma comprised between about 1.6 and about 2.2 times the volume to be augmented.

22. The method of claim 12, wherein said platelet gel is obtainable from said platelet-rich plasma clotted by adding calcium chloride and by treating at about 37° C.

23. The method of claim 12, wherein the amount of augmented soft tissue is a volumetric substitution of the amount of soft tissue removed from the patient.

* * * * *